United States Patent
Sugiyama et al.

(10) Patent No.: US 7,005,545 B2
(45) Date of Patent: Feb. 28, 2006

(54) PROCESS FOR PRODUCING FLUORINATED FLUOROSULFONYLALKYL VINYL ETHER

(75) Inventors: Akinari Sugiyama, Settsu (JP); Tatsuya Ohtsuka, Settsu (JP); Kazuyoshi Ichihara, Settsu (JP); Toshiya Mantani, Settsu (JP)

(73) Assignee: Daikin Industries, Ltd., Osaka (JP)

( * ) Notice: Subject to any disclaimer, the term of this patent is extended or adjusted under 35 U.S.C. 154(b) by 0 days.

(21) Appl. No.: 10/515,338

(22) PCT Filed: May 23, 2003

(86) PCT No.: PCT/JP03/06441

§ 371 (c)(1),
(2), (4) Date: Dec. 2, 2004

(87) PCT Pub. No.: WO03/106408

PCT Pub. Date: Dec. 24, 2003

(65) Prior Publication Data

US 2005/0177001 A1    Aug. 11, 2005

(30) Foreign Application Priority Data

Jun. 14, 2002  (JP) .............................. 2002-173702

(51) Int. Cl.
  *C07C 309/00*  (2006.01)
(52) U.S. Cl. .................................... 562/825
(58) Field of Classification Search ............... 562/825
See application file for complete search history.

(56) References Cited

U.S. PATENT DOCUMENTS 3,282,875 A  11/1966  Connolly et al. .......... 260/29.6
3,560,568 A   2/1971  Resnick .................... 260/513
4,511,518 A *  4/1985  Kimoto et al. ............. 562/825

FOREIGN PATENT DOCUMENTS

| | | |
|---|---|---|
| GB | 1034197 | 6/1966 |
| JP | 41-7949 | 4/1966 |
| JP | 57-28025 | 2/1982 |
| JP | 61-030552 | 2/1986 |
| JP | 61-30552 | 2/1986 |
| JP | 09-124588 | 5/1997 |
| JP | 9-124588 | 5/1997 |
| JP | 11-228474 | 8/1999 |
| JP | 11-335346 | 12/1999 |

OTHER PUBLICATIONS

International Search Report dated Sep. 2, 2003.

* cited by examiner

*Primary Examiner*—Paul A. Zucker
(74) *Attorney, Agent, or Firm*—Armstrong, Kratz, Quintos, Hanson & Brooks, LLP

(57) ABSTRACT

The present invention provides a process for producing a fluorinated fluorosulfonylalkyl vinyl ether represented by general formula (2):

$$CF_2=CFO(CF_2CF(CF_3)O)_nCF_2CF_2SO_2F \quad (2)$$

wherein n is an integer from 0 to 10, comprising fluorinating a perfluorovinylether sulfonate with $SF_4$ and HF, the perfluorovinylether sulfonate being represented by general formula (1):

$$CF_2=CFO(CF_2CF(CF_3)O)_nCF_2CF_2SO_3M \quad (1)$$

wherein M is Ma or $Mb_{1/2}$, provided that Ma is an alkali metal and Mb is an alkaline earth metal; and n is as defined above. According to the process of the invention, the fluorinated fluorosulfonylalkyl vinyl ether can be produced in high yield in an industrially advantageous manner.

2 Claims, No Drawings

PROCESS FOR PRODUCING FLUORINATED FLUOROSULFONYLALKYL VINYL ETHER

TECHNICAL FIELD

The present invention relates to a process for producing a fluorinated fluorosulfonylalkyl vinyl ether.

BACKGROUND ART

The fluorinated fluorosulfonylalkyl vinyl ether represented by the general formula: $CF_2=CFOCF_2CF_2SO_2F$ is a compound that is useful as a starting material for the industrial production of ion exchange membranes, etc.

For the production of a sulfonyl vinyl ether such as the fluorinated fluorosulfonylalkyl vinyl ether, British Patent No. 1,034,197 discloses a method of adding hexafluoropropylene oxide to $FCOCF_2SO_2F$ and then thermally decomposing the obtained sulfonyl fluoride derivative. In this method, when two or more molecules of hexafluoropropylene oxide are added to $FCOCF_2SO_2F$, a sulfonyl vinyl ether represented by $CF_2=CFO(CF_2CF(CF_3)O)_nCF_2CF_2SO_2F$ can be obtained. However, when one molecule of hexafluoropropylene oxide is added to $FCOCF_2SO_2F$, the main product is a cyclization product represented by the following formula:

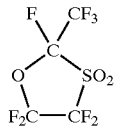

with the result that the fluorinated fluorosulfonylalkyl vinyl ether represented by $CF_2=CFOCF_2CF_2SO_2F$ can hardly be obtained.

Japanese Unexamined Patent Publication No. 1982-28025 discloses a method of adding chloropentafluoropropylene oxide to $FCOCF_2SO_2F$ and thereafter conducting thermal decomposition. This method can provide a fluorinated fluorosulfonylalkyl vinyl ether; however, chloropentafluoropropylene oxide, which is used as a starting material, cannot be obtained in high yield, so that the fluorinated fluorosulfonylalkyl vinyl ether cannot be efficiently produced at low cost.

Other attempts to produce sulfonyl vinyl ethers include a method of converting the halogen of a halogen-terminated vinyl ether to an $SO_2F$ group as disclosed in Japanese Unexamined Patent Publication No. 1986-30552; a method of dechlorinating $CF_2ClCFCOCF_2CF_2SO_2F$ using zinc, as disclosed in Japanese Unexamined Patent Publication No. 1999-228474; etc.

These methods, however, fail to give a good yield of sulfonyl vinyl ether, which is the intended product. Therefore, they are not satisfactory as industrial production methods.

U.S. Pat. No. 3,560,568 discloses a method of using $FCOCF(CF_3)OCF_2CF_2SO_2F$ as a starting material, forming its cyclization product, carrying out ring opening using $CH_3ONa$ to form $CF_2=CFOCF_2CF_2SO_3Na$, chlorinating the terminal $SO_3Na$ group with $PCl_5$ to synthesize $CF_2=CFOCF_2CF_2SO_2Cl$, and then fluorinating it with NaF to convert the $SO_2Cl$ group to an $SO_2F$ group. This method, however, is very inefficient since $CF_2=CFOCF_2CF_2SO_3Na$ shows extremely low chlorination reactivity. The method also has disadvantages such as the generation of HCl gas when water is present in the reaction system. In addition, the method requires the almost complete removal of impurities such as NaF before the chlorination reaction, and involves the difficulty of separating the by-product $POCl_3$ from the chlorination product $CF_2=CFOCF_2CF_2SO_2Cl$ by distillation. The production process is thus very complicated, making the industrial practice of this method very difficult.

DISCLOSURE OF THE INVENTION

The present invention has been achieved in view of the above-mentioned state of the art. A principal object of the present invention is to provide a process for producing a fluorinated fluorosulfonylalkyl vinyl ether in high yield in an industrially advantageous manner.

The present inventors conducted extensive research in order to solve the above-mentioned problems. As a result, they found that the method of fluorinating a specific perfluorovinylether sulfonate derivative as starting material with $SF_4$ and HF enables the preparation of a fluorinated fluorosulfonylalkyl vinyl ether in high yield by a relatively convenient process. Based on this finding, the present invention has been accomplished.

The present invention provides a process for producing a fluorinated fluorosulfonylalkyl vinyl ether represented by general formula (2):

$$CF_2=CFO(CF_2CF(CF_3)O)_nCF_2CF_2SO_2F \quad (2)$$

wherein n is an integer from 0 to 10, comprising fluorinating a perfluorovinylether sulfonate with $SF_4$ and HF, the perfluorovinylether sulfonate being represented by general formula (1):

$$CF_2=CFO(CF_2CF(CF_3)O)_nCF_2CF_2SO_3M \quad (1)$$

wherein M is Ma or $Mb_{1/2}$, provided that Ma is an alkali metal and Mb is an alkaline earth metal; and n is as defined above.

The perfluorovinylether sulfonate of general formula (1):

$$CF_2=CFO(CF_2CF(CF_3)O)_nCF_2CF_2SO_3M \quad (1)$$

wherein M is Ma or $Mb_{1/2}$, provided that Ma is an alkali metal and Mb is an alkaline earth metal; and n is an integer from 0 to 10, which is used as a starting material in the method of the invention, is a known compound. It can be prepared by methods disclosed in, for example, U.S. Pat. No. 3,560,568, Japanese Unexamined Patent Publication No. 2001-114750, etc.

In general formula (1), examples of alkali metals include Na, K, Li, Cs, etc. Examples of alkaline earth metals include Ca, Mg, etc.

According to the process of the present invention, the fluorinated fluorosulfonylalkyl vinyl ether represented by general formula (2):

$$CF_2=CFO(CF_2CF(CF_3)O)_nCF_2CF_2SO_2F \quad (2)$$

wherein n is as defined above can be produced by fluorinating the perfluorovinylether sulfonate of general formula (1) with $SF_4$ and HF.

Although the fluorination conditions are not restricted, the reaction temperature is usually about 20° C. to about 200° C., preferably about 20° C. to about 100° C., and the reaction time is about 0.5 to about 48 hours, preferably about 1 to about 20 hours.

$SF_4$ is used in an amount of about 1 to about 10 moles, and preferably about 1 to about 5 moles, per mole of reaction substrate. HF is used in an amount of about 2 to about 1000 moles, and preferably about 2 to about 500 moles, per mole of $SF_4$.

Although the above reaction can be performed in a solvent, the use of a solvent is not necessarily required since HF, if added in large excess, can also act as a solvent. There are no restrictions on the solvent, and any solvent that does not participate in the reaction may be used. Examples thereof include organic solvents such as methylene chloride, chloroform, diethyl ether, hydrofluorocarbons, hydrochlorofluorocarbons, fluorine-containing oils, etc.

The concentration of compound (1) in the solvent is not limited, and is usually about 10 to about 100 mass %.

Following the above method, the fluorinated fluorosulfonylalkyl vinyl ether of general formula (2) can be obtained.

The obtained crude compound is purified by known methods such as extraction, distillation, recrystallization, column chromatography, etc.

The fluorinated fluorosulfonylalkyl vinyl ether of general formula (2) obtained by the process of the invention is useful as a monomer component for polymers used for electrolyte membranes or ion exchange membranes.

Electrolyte membranes or ion exchange membranes are used as electrolyte membranes of solid polymer electrolyte fuel cells, various membranes for applications such as lithium batteries, brine electrolysis, water electrolysis, hydrohalic acid electrolysis, oxygen concentrators, humidity sensors, gas sensors, etc.

As described above, the process of the present invention achieves a high yield of the intended fluorinated fluorosulfonyl ether at low cost in an industrially advantageous manner without requiring complicated operations.

BEST MODE FOR CARRYING OUT THE INVENTION

The present invention is described in more detail with reference to the following Example.

EXAMPLE 1

5.12 g (0.017 mol) of $CF_2\!\!=\!\!CFOCF_2CF_2SO_3Na$ was placed into a 100 ml SUS autoclave (with an inner tube made of PTFE resin) and cooled in an ice bath. In the autoclave, the air is evacuated, and then 50 g (2.5 mol) of HF and 6.5 g (0.06 mol) of $SF_4$ were added. The temperature was increased to room temperature, and the mixture was stirred for 16 hours to carry out a reaction.

After the reaction, 30 ml of water was added while the reactor was ice-cooled. The liquid in the autoclave was taken out to obtain a reaction mixture, and the inside of the autoclave was then washed with a further 30 ml of water, which was added to the reaction mixture. Using a separatory funnel made of PFA resin, the lower liquid phase was recovered, giving 3.9 g of $CF_2\!\!=\!\!CFOCF_2CF_2SO_2F$ (yield: 85%).

The invention claimed is:

1. A process for producing a fluorinated fluorosulfonylalkyl vinyl ether represented by general formula (2):

$$CF_2\!\!=\!\!CFO(CF_2CF(CF_3)O)_nCF_2CF_2SO_2F \qquad (2)$$

wherein n is an integer from 0 to 10, comprising fluorinating a perfluorovinylether sulfonate with $SF_4$ and HF, the perfluorovinylether sulfonate being represented by general formula (1):

$$CF_2\!\!=\!\!CFO(CF_2CF(CF_3)O)_nCF_2CF_2SO_3M \qquad (1)$$

wherein M is Ma or $Mb_{1/2}$, provided that Ma is an alkali metal and Mb is an alkaline earth metal; and n is as defined above.

2. A process for producing a fluorinated fluorosulfonylalkyl vinyl ether according to claim 1, wherein $SF_4$ is used in an amount of 1 to 10 moles per mole of perfluorovinylether sulfonate of general formula (1), and HF is used in an amount of 2 to 1000 moles per mole of $SF_4$.

* * * * *